United States Patent [19]

Tokuno et al.

[11] Patent Number: 4,737,846
[45] Date of Patent: Apr. 12, 1988

[54] DEVICE FOR DETECTING DEFECTS IN SINGLE FACED CORRUGATED FIBERBOARDS

[75] Inventors: Masateru Tokuno, Nishinomiya; Tetsuya Sawada, Kyoto; Yasuharu Mori, Nishinomiya; Ikuo Yoshimoto, Moriguchi, all of Japan

[73] Assignee: Rengo Co., Ltd., Osaka, Japan

[21] Appl. No.: 54,923

[22] Filed: May 28, 1987

[30] Foreign Application Priority Data

May 29, 1986 [JP] Japan ................. 61-126851

[51] Int. Cl.⁴ ............................................ H04N 7/18
[52] U.S. Cl. .................................... 358/106; 358/101
[58] Field of Search ................. 358/93, 101, 106, 107; 250/222.1, 572; 356/237; 382/8

[56] References Cited

U.S. PATENT DOCUMENTS

| | | |
|---|---|---|
| 3,419,677 | 12/1968 | Fiori ..................................... 358/106 |
| 4,292,672 | 9/1981 | Southgate ........................... 358/106 |
| 4,385,700 | 5/1983 | Hodges ............................. 250/222.1 |
| 4,460,921 | 7/1984 | Henry ................................... 358/106 |

Primary Examiner—Howard W. Britton
Attorney, Agent, or Firm—Armstrong, Nikaido, Marmelstein & Kubovcik

[57] ABSTRACT

A device for detecting any defects in single faced corrugated fiberboard while it is running. A light is irradiated to the corrugated surface of the fiberboard and the striped image is scanned by an image pick-up unit and the picture signal is converted to binary-coded signal to discriminate the number of stripes or corrugations. The number is counted by a counter and compared with a normal number by a microcoputer. If there is too large a difference between them, the scanned part is judged as defective. This device can detect any defects in a running web at a sufficiently high speed to follow the line speed of a corrugating machine.

6 Claims, 5 Drawing Sheets

Error signal k
Binary-coded signal d
Cursor signal j

DEVICE FOR DETECTING DEFECTS IN SINGLE FACED CORRUGATED FIBERBOARDS

The present invention relates to a device for detecting defects in single faced corrugated fiberboards.

Normally, corrugated fiberboards are produced continuously at high speed by a corrugating machine on which a first linerboard is bonded to the top at one side of flutes of a corrugated medium to form a single faced corrugated fiberboard to which a second linerboard is bonded to the top at the other side of flutes of corrugated medium.

In corrugated fiberboards thus produced, various kinds of defective parts resulting from the defects in the corrugating medium are often found out, for example, there are found such defects as partial peeling due to poor bonding between the first linerboard and the corrugated medium, irregular corrugations resulting from the flaws or blisters on the corrugated medium formed after the formation of flutes, spots or stains on the corrugated medium, and irregular corrugations due to the tapes applied for splicing the corrugating medium in a paper making process or corrugating process or due to the overlapping of corrugating mediums at their spliced points. It is important to assure high quality to remove such defective parts during the proces of production of corrugated fiberboards.

However, due to the fact that corrugated fiberboards are not only mass-produced continuously at high speed but also another linerboard is bonded to a single faced corrugated fiberboard having one side of the corrugating medium exposed to the atomosphere to cover the corrugating medium, no effective measures for detecting such defective areas during the production process have been taken.

It is an object of the present invention to provide a device for detecting defects in corrugating mediums during the production process of corrugated fiberboards. In the device, a corrugating medium with its one side laminated by a linerboard is irradiated by light at the exposed top of its flutes, and the striped shadow images projected are picked up and electronically processed to detect any defective areas.

According to the present invention, striped shadow images of a single faced corrugated fiberboard are picked up for a period of one cycle defined by the emission of a stroboscope or by the opening and closing of a shutter, and processed so as to discriminate defectives from nondefectives. Therefore, the defective areas are detected rapidly enough to keep up with the high speed of the production line in the course of production of corrugated fiberboards. Thus the device according to the present invention contributes to the improvement in quality of end products.

Other features and objects of the present invention will become apparent from the following description taken with reference to the accompanying drawings, in which.

<FIRST EMBODIMENT>

Figure 1:
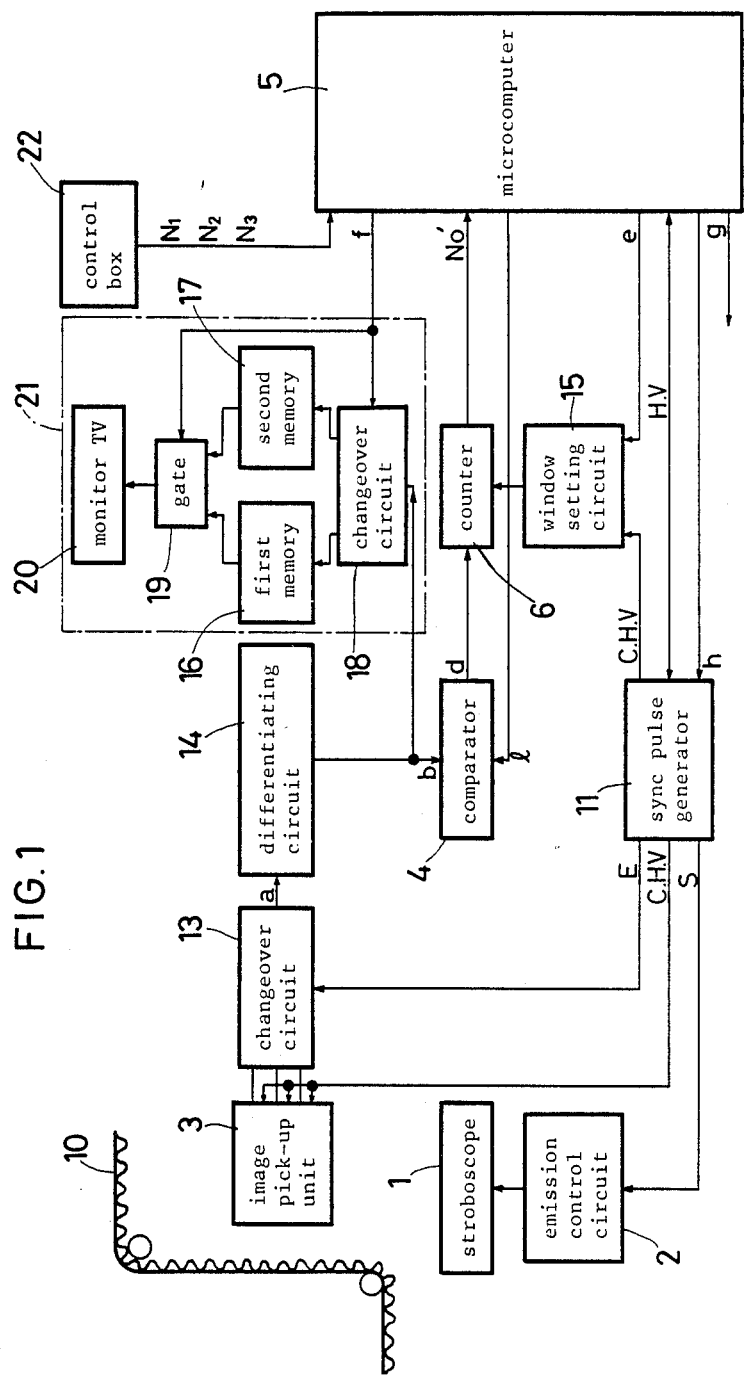
FIG. 1 is a block diagram of the first embodiment in accordance with the present invention.
Figure 2:
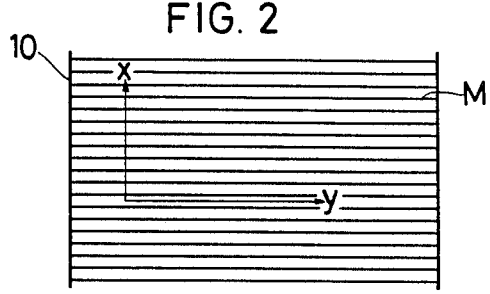
FIG. 2 is a front view of a portion of a shadow image.

In the first embodiment of the present invention shown in FIG. 1, a single faced corrugated fiberboard 10 formed by bonding a linerboard to a corrugating medium is fed vertically at a part of its way. A stroboscope 1 and its emission control circuit 2 are provided near the area where the single faced corrugated fiberboard 10 is fed vertically. The stroboscope 1 emits flash lights obliquely with respect to the flutes of corrugating medium of the single faced corrugated fiberboard 10 so as to produce striped shadow images M (FIG. 2). If there is no defective area in the corrugating medium, the shadow image M appears without any irregularity. If there is, the stripes at the defective area will appear irregular with their number per unit length above or below normal. The device according to the present invention is adapted to compare the actual count for the number of stripes with a normal number of the stripes so as to detect any defective areas.

A stroboscope trigger signal S from a synchronizing pulse generating circuit 11 controls the emission control circuit 2 to cause the stroboscope 1 to emit a flash light.

A plurality of image pick-up units 3 are arranged in a line horizontally (in a direction parallel with the flutes of the corrugating medium), facing the surface of the single faced corrugated fiberboard 10 running vertically. Each image pick-up unit 3 comprises a charge coupled device (CCD) camera arranged so that its horizontal scanning direction X will correspond to the direction normal to the flutes and its vertical scanning direction Y will correspond to the direction parallel to the flutes. (FIG. 2) The image pick-up units 3 scan the images by the interlaced scanning in response to clock signals C, horizontal synchronizing signals H and vertical synchronizing signals V from the synchronizing pulse generating circuit 11 to produce picture signals in time series. In some cases, these signals may be generated within the image pick-up units 3.

Figure 3:
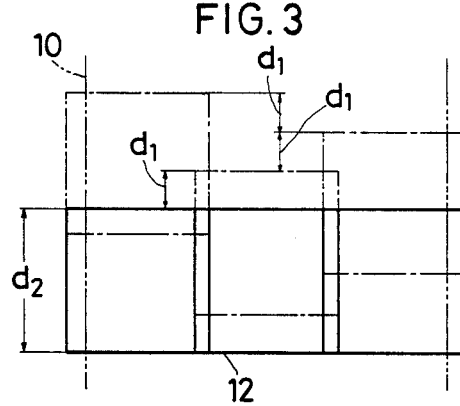
FIG. 3 is a plan view showing how the camera windows cover the fiberboard.

The coverage of a camera window 12 of a single image pick-up unit 3 is usually narrower than the width of the single faced corrugated fiberboard 10 as shown in FIG. 3. Therefore, a plurality of image pick-up units 3 are used. The number of the units is determined according to the width of the fiberboard 10. In this embodiment, three image pickup units are used.

The camera windows 12 of the image pick-up units 3 are so positioned as to partially overlap with one another in order to leave no unscanned areas in the direction of width. The image pick-up units 3 are changed over from one to another by turns by a changeover circuit 13. Among three pick-up units 3, the camera windows 12 of each unit 3 scan the zone which is behind the zone scanned by the camera window of the preceding unit by a distance $d_l$, which is the distance covered by the running web of the single faced corrugated fiberboard 10 within the time required to scan one frame. The relationship between the distance $d_1$ and a distance $d_2$ (which is the length of camera window 12 in the direction of movement of the fiberboard 10) should be set at $d_1 < d_2/3$. This assures that the distance covered by the single faced corrugated fiberboard 10 from the beginning of scanning by the first camera window 12 to the end of scanning by the third one will not exceed the distance $d_2$. Thus, no unscanned area will be left with respect to the direction of running of the fiberboard.

Figure 4:
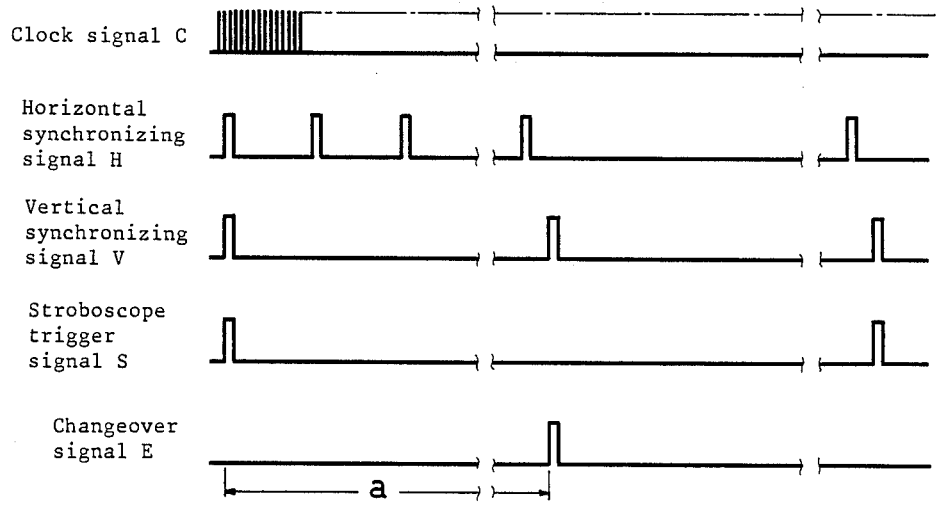
FIG. 4 is a diagrammatic view showing the relationship among the pulse signals in the first embodiment.

FIG. 4 shows the relationship among the signals. Clock signals C are generated for each picture element. Two vertical synchronizing signals V are generated per horizontal synchronizing signals H for one frame. One stroboscope trigger signal S and one changeover signal E are generated per two vertical synchronizing signals V. The stroboscope trigger signals S are synchronized with the first pulses of the vertical synchronizing signals V, while the change-over signals E are synchronized with the second ones. Each changeover signal E is transmitted in response to a changeover command signal h from a microcomputer 5.

When in response to the abovesaid signals the stroboscope 1 flashes, the image pick-up units 3 can catch a shadow image. The picture signals a for one field scanned by the horizontal synchronizing signal H and the first pulse of the vertical synchronizing signal V are taken in through the changeover circuit 13. Since the image pick-up units 3 are changed over by the changeover signals E synchronized with the second pulses of the vertical synchronizing signals V, the picture signals for the remaining one field are not taken. Namely, it is only the picture signals a for one field picked up by interlaced scanning that are taken in through the changeover circuit 13.

Although it is preferable to take in the picture signals for one frame in order to obtain a higher resolution, it is more desirable to take in the picture signals only for one field as described above because this allows to use the scanning time for the remaining one field for the discrimination of defectives from nondefectives, thus making it possible to increase the detection speed. The influence of the deterioration in resolution is practically negligible.

The picture signals a are inputted in a differentiating circuit 14, which is not essential but should be provided in order to pick out the variations in signals and improve the detection accuracy.

The picture signals b treated in the differentiating circuit 14 is inputted in a comparator 4, which is supplied with a threshold level value l from the microcomputer 5 and converts the picture signals b to binary-coded signals d in comparison with the threshold level value l.

A counter 6 counts the number of binary-coded signals d for each picture element line (in one horizontal scanning line), the number being equal to the number of stripes. The count $N_0'$ is read into the microcomputer 5 in response to a horizontal synchronizing signal H.

Each changeover command signal h is transmitted from the microcomputer 5 in response to the second pulse of the vertical synchronizing signals V after the count $N_0'$ for one field has been read into the microcomputer 5.

During this operation, the microcomputer 5 may supply a window setting circuit 15 with a designating signal e to specify the area to be counted in the area scanned by the camera window 12 of each image pick-up unit 3. The window setting circuit 15 receives the clock signals C, horizontal synchronizing signals H and vertical syncronizing signals V from the circuit 11. In response to these signals and the designating signal e, the counter 6 counts the number of the binary-coded signals for the specified area only, and outputs the count $N_0'$ to the micricomputer 5.

In order to monitor the picture signals b for the defective areas, there is provided a monitoring system 21 including a first memory 16 and a second memory 17, a changeover circuit 18, a gate 19 and a monitor TV 20. A changeover signal f from the microcomputer 5 switches from the first memory 16 to the second one 17 so as to store the picture signal b and display them on the monitor TV 20 through a gate 19. While no changeover signal f is supplied, the picture signals b are stored in the first memory 16 continuously and displayed on the monitor TV 20.

In the drawings, numeral 22 designates a control box, which is used to set a maximum allowable number $N_1$, a maximum allowable number $N_2$ for error scanning lines and a maximum allowable accumulated error number $N_3$ in the microcomputer.

The maximum allowable number $N_1$ means a maximum allowable difference between a preset normal number $N_0$ of stripes and an actual counted number $N_0'$ of stripes in one horizontal scanning line.

If a plurality of scanning lines appear successively, each having stripes in which the difference between the actual counted number $N_0'$ and the preset normal number $N_0$, that is, $|N_0'-N_0|$ is more than $N_1$, this is judged to be due to flaws, blisters or stains and the scanned area is decided as "defective".

The maximum allowable number $N_2$ for the number of error scanning lines is a maximum allowable number of scanning lines that appear successively in the picture image for one field, each exceeding the maximum allowable number $N_1$. If the number of such scanning lines is below $N_2$, the scanned area is regarded as nondefective. Such scanning lines will be hereinafter called "error scanning lines".

Even if a "good" decision is made due to the fact that the number of error scanning lines appearing consecutively is below the maximum allowable number $N_2$, large defect factors may be concentrated in a very narrow area, so that the difference $|N_0'-N_0|$ is too large to be regarded as nondefective. Therefore, if a plurality of error scanning lines appear successively, each exceeding $N_1$, it is preferable to count the difference $|N_0'-N_0|$ for each scanning line and accumulate each counted number of difference successively. The scanned area is decided as "defective" if the accumulated number exceeds a predetermined number. The abovesaid maximum allowable accumulated error number $N_3$ is the maximum allowable number for the number obtained by accumulating the difference $|N_0'-N_0|$ for the succesive scanning lines, if a plurality of scanning lines each exceeding the number $N_1$ appear successively.

According to the criterion of the extent of the defects to which a product is acceptable as nondefective, both $N_2$ and $N_3$ may be taken into consideration in discriminating nondefective from defectives or either one of the two may be considered.

Various other methods may be adopted to distinguish nondefectives from defectives. In practice, the numbers $N_1$, $N_2$ and $N_3$ are preset, taking into consideration the extent of defects to which a product may be regarded as a nondefective or the range which may be regarded as a control error.

Next, it will be described how the microcomputer 5 functions to discriminate any defective areas. One of the image pick-up units 3 is used to record a normal number of stripes (preset number $N_0$) contained in the picture image for one field where there are no defective parts in a corrugating medium, and teach the microcomputer 5 the preset number beforehand. The maximum allowable members $N_1$, $N_2$ and $N_3$ are also inputted through the control box 22.

Figure 5:
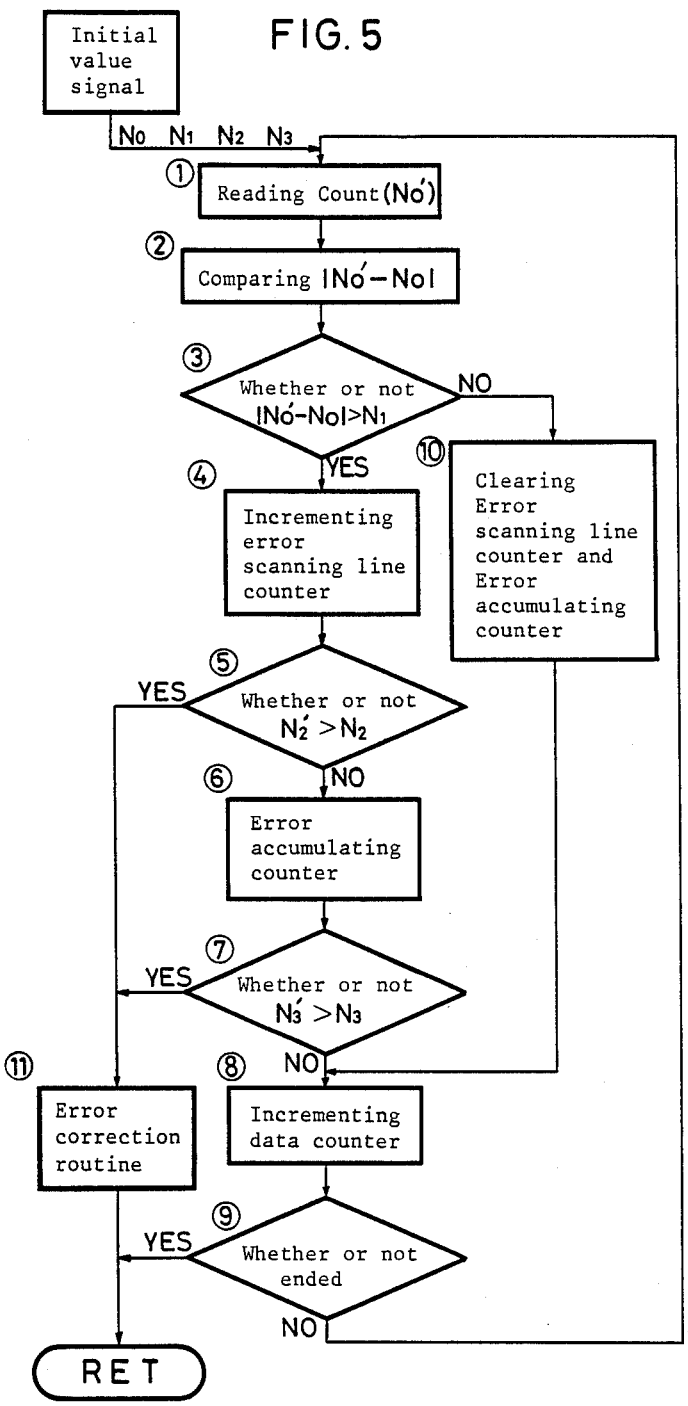
FIG. 5 is a flow chart showing the process of discrimination in the microcomputer.

In the microcomputer 5, the count or number count $N_0$ inputted from the counter 6 is read out (Step 1 in FIG. 5 to compare it with the preset number $N_0$ (Step 2). Then, it is decided whether or not the difference $|N_0'-N_0|$ is larger than the maximum allowable number $N_1$ (Step 3). If it is, an error scanning line counter is incremented (Step 4). It is then judged whether or not the incremented number of error scanning lines $N_2'$ is larger than the maximum allowable number $N_2$ (Step 5). If it is smaller, the error of difference $|N_0'-N_0|$ is accumulated by an error accumulation counter (Step 6). It is then decided whether or not the accumulated error $N_3'$ is larger than the maximum allowable number $N_3$ (Step 7). If smaller, a data counter is incremented (Step 8). Next, the incremented number in the data counter is compared with the number of scanning lines for one field in order to decide whether or not the examination for one field has ended (Step 9). If not, the discrimination procedure for the next scanning line is resumed from the start.

In Step 3, every time the difference between the preset number $N_0$ and the counted number $N_0'$ that is, $|N_0'-N_0|$ is smaller than the maximum allowable number $N_1$ both the error scanning line counter and the error accumulation counter are cleared (Step 10). And then the data counter is incremented.

If, in Step 5, the number of error scanning lines $N_2'$ is larger than the maximum allowable number $N_2$, which shows that too many error scanning lines had appeared in succession, the scanned area will be decided as "defective", judging that there are defect factors existing over a wide area even though the error or difference $|N_0'-N_0|$ for each error scanning line is comparatively small. In this case, the system is passed to the error correction routine (Step 11). If, in Step 7, the accumulated error number $N_3'$ is larger than the maximum allowable number $N_3$, which suggests that there exists rather large defect factors in a limited area even though the number $N_2'$ of error scanning lines is relatively small, the procedure is switched to the error correction routine (Step 11).

The microcomputer 5 transmits a defect signal g and a monitor memory circuit changeover signal f to start the error correction. The above signals cause the alarm to operate or cause the second memory 17 of the monitoring system 21 to temporarily store the picture signals to display the picture of the defective part on the monitor TV 20.

Upon completion of the error correction and the discrimination steps, the procedure returns to the start (RET) for the next detection operation.

Figure 6:
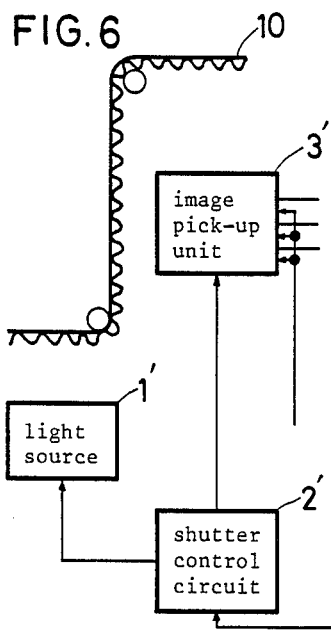
FIG. 6 is a block diagram showing a variation of the first embodiment.

If, as shown in FIG. 6, image pick-up units 3' provided with high-speed shutters such as electromagnetic shutters are used in place of the image pick-up units 3 used in this embodiment, a standard light source 1' and a shutter control circuit 2' are used and the shutters of the image pick-up units 3' are opened and closed. The other arrangement is the same as above.

<SECOND EMBODIMENT>

Figure 7:
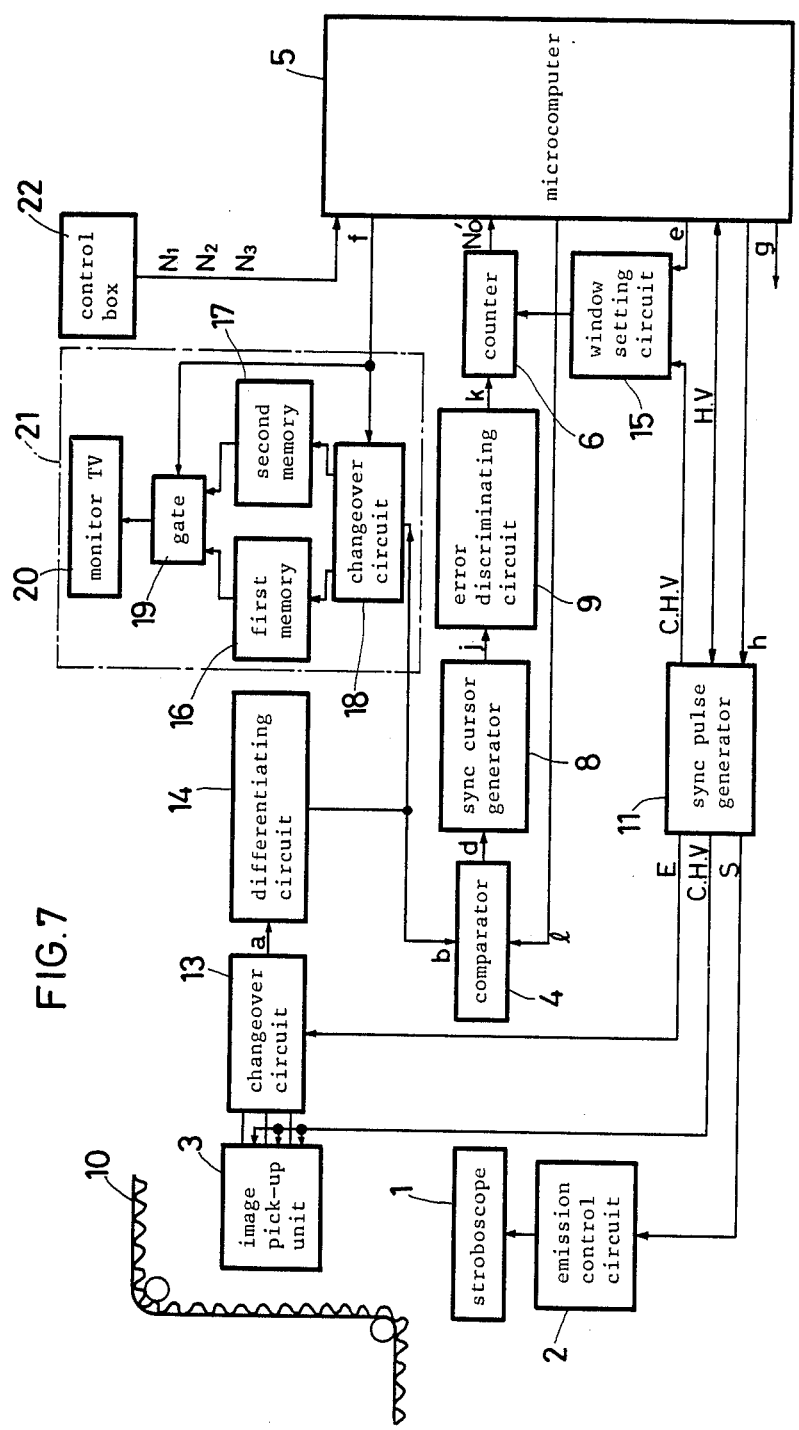
FIG. 7 is a block diagram of the second embodiment.

The second embodiment shown in FIG. 7 is substantially the same as the first embodiment except that a synchronized cursor generating circuit 8 and an error discriminating circuit 9 are provided between the comparator 4 and the counter 6. The image pick-up units 3' provided with the shutters may be used in this embodiment as in the first embodiment.

Figure 8:
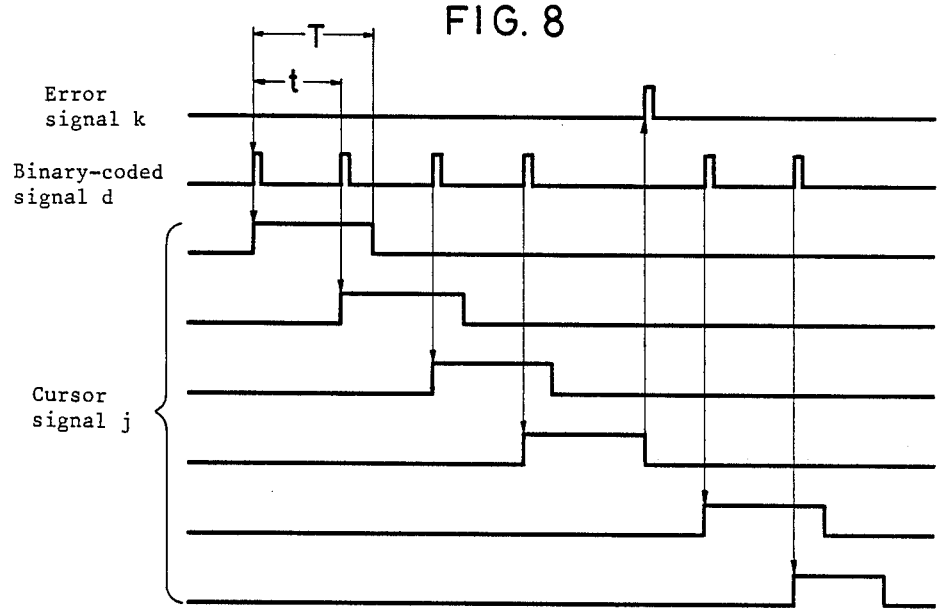
FIG. 8 is a diagrammatic view showing the relationship among the pulse signals in the second embodiment.

The synchronized cursor generating circuit 8 generates a cursor signal j synchronized with a binary-coded signal d transmitted from the comparator 4 (see FIG. 8). The cursor signal j is a pulse signal having a period T which is longer than a fixed period t of the binary-coded signal d when it is normal and is shorter than the period 2t.

The cursor signal j is inputted in the error discriminating circuit 9 which monitors the presence of the cursor signal j so as to transmit an error signal K if the cursor signal j is interrupted.

The counter 6 counts the error signal k and inputs the counted number $N_0'$ into the microcomputer 5. The discrimination procedure in the microcomputer 5 in this embodiment is the same as shown in FIG. 5 except that the preset number $N_0$ is replaced with another number $N_{01}$. Namely, in this embodiment, the maximum allowable number of error signals K included in one scanning line is preset as $N_{01}$ and the counted number $N_0'$ of error signals K is compared with $N_{01}$ to decide whether it is allowable or not. Therefore, the flow chart of the second embodiment is different from the one of FIG. 5 only in that $N_0$ is replaced with $N_{01}$.

What is claimed is:

1. A device for detecting defects in a web of single faced corrugated fiberboard while it is running, said device comprising:
   a light source disposed near the track of said web for irradiating a light to the corrugated surface of said web to produce a striped image;
   an image pick-up means for scanning the striped image at a predetermined period by interlaced scanning in a direction perpendicular to the stripes on the striped image to convert the striped image to picture signals and giving the picture signals in a time series manner in synchronization with said period;
   a comparator means for converting said picture signals to binary-coded signals, the number of which corresponds to the number of stripes;
   a counter for counting the binary-coded signals; and
   a computer for comparing the count from said counter with a preset number to detect defects in the single faced corrugated fiberboard.

2. The device as claimed in claim 1, wherein said light source is a stroboscope controlled by signals produced at predetermined time intervals.

3. The device as claimed in claim 1, wherein said image pick-up means is provided with a shutter, the opening of which is controlled by signals produced at predetermined time intervals.

4. The device as claimed in claim 1 further comprising a synchronized cursor generating means for generating cursor signals synchronized with said binary-coded signals and having a predetermined width, an error discriminating means for receiving said cursor signals to discriminate error to produce an error signal, said counter means counting said error signals.

5. The device as claimed in claim 4, wherein said light source is a stroboscope controlled by signals produced at predetermined time intervals.

6. The device as claimed in claim 4, wherein said image pick-up means is provided with a shutter, the opening of which is controlled by signals produced at predetermined time intervals.

* * * * *